(12) United States Patent
Pilotaz et al.

(10) Patent No.: US 8,772,337 B2
(45) Date of Patent: Jul. 8, 2014

(54) PRESERVATIVE-FREE PROSTAGLANDIN-BASED OPHTHALMIC SOLUTION

(75) Inventors: Frederic Pilotaz, Vaulanaveys le Haut (FR); Fabrice Mercier, Clermont Ferrand (FR); Henri Chibret, Joze (FR)

(73) Assignee: Laboratoires Thea (FR)

(*) Notice: Subject to any disclaimer, the term of this patent is extended or adjusted under 35 U.S.C. 154(b) by 1030 days.

(21) Appl. No.: 12/666,778

(22) PCT Filed: Jul. 17, 2008

(86) PCT No.: PCT/FR2008/051347
§ 371 (c)(1),
(2), (4) Date: Dec. 24, 2009

(87) PCT Pub. No.: WO2009/013435
PCT Pub. Date: Jan. 29, 2009

(65) Prior Publication Data
US 2010/0210720 A1 Aug. 19, 2010

(30) Foreign Application Priority Data
Jul. 20, 2007 (FR) ...................................... 07 05272

(51) Int. Cl.
*A61K 31/5575* (2006.01)

(52) U.S. Cl.
USPC .......................................... 514/530; 514/573

(58) Field of Classification Search
USPC .................................................. 514/530, 573
See application file for complete search history.

(56) References Cited

U.S. PATENT DOCUMENTS

| 4,431,833 A | 2/1984 | Lodhi et al. |
| 5,886,035 A | 3/1999 | Shirasawa et al. |
| 2004/0082660 A1 | 4/2004 | Ueno |
| 2006/0199863 A1 | 9/2006 | Kimura et al. |
| 2006/0205725 A1 | 9/2006 | Ueno |
| 2010/0255104 A1* | 10/2010 | Nunez et al. .................. 424/489 |

FOREIGN PATENT DOCUMENTS

| EP | 0850926 A2 | 7/1998 |
| EP | 1666043 A1 | 6/2006 |
| WO | 9112008 A1 | 8/1991 |

* cited by examiner

*Primary Examiner* — Zohreh Fay
(74) *Attorney, Agent, or Firm* — St. Onge Steward Johnston & Reens LLC

(57) ABSTRACT

The present invention provides an ophthalmic solution without an antimicrobial preservative. The solution includes as an active substance at least one prostaglandin and as a solubilizing agent, a surfactant, where the solubilizing agent is polyoxyl-15-hydroxystearate.

14 Claims, 4 Drawing Sheets

PRESERVATIVE-FREE PROSTAGLANDIN-BASED OPHTHALMIC SOLUTION

CROSS REFERENCE TO RELATED APPLICATIONS

This is the United States national phase under 35 U.S.C. §371 of International Patent Application No: PCT/FR2008/051347 filed Jul. 17, 2008 which claims the benefit of French Patent Application No. 0705272 filed Jul. 20, 2007.

FIELD OF THE INVENTION

The invention concerns an ophthalmic solution containing at least one prostaglandin as its active substance, the said solution containing no antimicrobial preservative, in particular no quaternary ammonium preservative (e.g. benzalkonium chloride (BAC)).

BACKGROUND OF THE INVENTION

In the rest of the description, "antimicrobial preservative" or "antimicrobial" is taken to mean a preservative with antimicrobial properties, i.e. a compound capable of guaranteeing protection of the ophthalmic solution from possible microbial contamination. As far as the invention is concerned such agents should be distinguished from preservative agents involved in preserving the chemical characteristics of the solution such as antioxidants e.g. EDTA.

Prostaglandins are well known active substances administered to humans or animals via the topical route in the form of ophthalmic solutions for the treatment of glaucoma. The usual dosage for these formulations is 1 drop per day in both eyes, bearing in mind that prostaglandins may also be used in combination with a second anti-glaucoma agent such as a beta-blocker, a carbonic anhydrase inhibitor or an alpha-adrenergic agonist.

The prime disadvantage of prostaglandins is that they are not water soluble, so that incorporating them into an ophthalmic solution requires a preliminary solubilization step. Moreover, another constraint on making the formulation is the requirement to provide an ophthalmic solution which is chemically stable over time, in practice for a period of between 18 and 24 months. Another characteristic required of the ophthalmic solution is that it has to be stable relative to the packaging in which it is stored, in particular relative to packaging in low-density polyethylene (LDPE) material.

Currently, most prostaglandin based ophthalmic solutions on the market contain a preservative agent which, besides having antimicrobial properties, also solubilizes the active substance and partly stabilizes it. An example of such a solution is the product marketed under the trade name of Xalatan® by Pfizer, combining latanoprost and 0.02% by weight BAC. It should be noted that, despite the presence of BAC, this ophthalmic solution is not stable at ambient temperature and must be stored in the cold at a temperature of about 5° C. Moreover, Allergan markets an ophthalmic solution under the trade name of Lumigan® combining bimatoprost and 0.005% by weight BAC.

However, the use of antimicrobial preservatives, particularly BAC, in opthalmology for long-term treatment, as is the case particularly for glaucoma, is advised against in many publications because of problems with tolerance (see in this respect: "The New Class of Ophthalmic Agents: Here's how to choose the right prostaglandin for each patient" by J. James Thimons, O.D., F.A.A.O.—Optometric Management, May issue 2002). It is thus already established that antimicrobial preservative agents are toxic in long-term use, with the result that today there is a tendency to limit their use by reducing their concentration in ophthalmic solutions as much as possible, or better still, eliminating them from formulations.

This issue has been considered in the document WO 97/29752, which discloses use in place of part of the BAC of a non-ionic agent such as Cremophor®. In the formulation proposed, the concentration of BAC is limited to 0.01% by weight, the concentration of Cremophor® EL being 0.05% by weight. A product called Travatan® is on the market combining travoprost, BAC and Creinophor®, marketed by the company Alcon, owner of the patent application WO/9729752.

Polysorbate 80 has also been used in ophthalmic solutions as a partial substitute for BAC, as is the case for the product marketed under the trade name of Rescula®, for example, by Novartis, combining unoprostone with a mixture of BAC and polysorbate 80 forming 0.015% by weight of the solution.

Documents EP 1 321 144 and EPI 666 043 describe the capacity of polysorbate 80 to slow to a greater or lesser extent the adsorption of a specific prostaglandin, tafluprost, onto polyethylene (PE), low density polyethylene (LDPE), polypropylene (PP), polyethylene terephthalate (PET) or a mix of PET/polyarylate forming the packaging. No indication is given of the possible capacity of polysorbate 80 to stabilize the solution over time for a period of 18 to 24 months. These documents contain no examples of ready-to-use ophthalmic solutions and simply state that a certain number of additives may be added to the prostaglandin and polysorbate 80 combination, for example preservatives such as BAC. Nothing in this document indicates that BAC or preservatives in general are expressly excluded from the final composition.

Document US2004/0082660 describes an ophthalmic solution without BAC containing a mixture of latanoprost and polysorbate 80 (table 1, test 2). The results given characterize the homogeneity of the solution obtained 30 minutes after 7 hours of agitation, i.e. the capacity of polysorbate 80 to solubilize latanoprost in 7 hours. No indication is given concerning the chemical stability of the solution over time.

Document EP 0850 926 describes ophthalmic solutions combining prostaglandin, polysorbate 80 and glycerine. No indication is given concerning the solubility of the prostaglandin or the chemical stability of the solution over time and relative to the packaging.

SUMMARY OF THE INVENTION

The invention therefore proposes to resolve the problem of developing a prostaglandin based formulation free of any antimicrobial preservative which is stable over time in solution at ambient temperature (over a period of 18 to 24 months), and is also stable in the plastic packaging material in which it is usually stored, in particular LDPE packaging.

Another objective is to propose a formulation sufficiently fluid to be sterilized by filtration and packed using a 'blow-fill-seal' aseptic packaging technique.

The applicant has found that substituting Solutol HS15 for the polysorbate 80 solves the problem of the stability of prostaglandins over time and relative to the primary packaging, in particular LDPE packaging.

The CAS name of Solutol HS15 is polyoxyl-15-hydroxystearate and the CAS number 70142-34-6. This product, marketed under the name of Solutol® HS15 also has a monograph in the European Pharmacopoeia identified by the name Macrogol 15 hydroxystearate.

It should be noted that Solutol® HS15 is described in the document WO 91/12008 in an ophthalmic composition combined with an antibiotic belonging to the macrolide family, particularly primycin.

The applicant has found very surprisingly that besides conferring stability at ambient temperature on the solution obtained for at least 18 months, the use of Solutol® HS 15 as a prostaglandin solubilizing agent in an ophthalmic solution also confers stability relative to the packaging, in particular LDPE type plastic packaging of European Pharmacopoeia (EP) quality, which is used as sterile product packaging and is manufactured from additive-free polyethylene.

The invention thus concerns a ready-to-use ophthalmic solution without antimicrobial preservative including as active substance at least one prostaglandin and as solubilizing agent, a surfactant, characterized by the solubilizer being polyoxyl-15-hydroxystearate.

According to a first characteristic, the concentration of the solubilizing agent (Solutol® HS 15) in the solution is between 1 and 20 WI, to advantage between 2 and 10 WI.

Below the concentration of 0.1% (m/v), the solubilizing effect is incomplete. Above 2% (m/v), no noticeable improvement in solubilization is seen.

According to another characteristic, the prostaglandin concentration in the solution is between 0.02 and 1.5 g/l.

In practice, there is at least one prostaglandin in the solution and the prostaglandins are selected from the group comprising 17-phenyl-13,14 dihydro trinor prostaglandin $F_{2\alpha}$ isopropyl ester (latanoprost), 20-ethyl prostaglandin $F_{2\alpha}$, (+)-fluprostenol isopropyl ester (travoprost), 17-phenyl trinor prostaglandin $F_{2\alpha}$ amide, 17-phenyl-13,14 dihydro trinor prostaglandin $F_{2\alpha}$ ethyl amide (bimatoprost), tafluprost prostaglandin $F_{2\alpha}$ ethanolamide, bimatoprost (free acid)-$d_4$, bimatoprost-$d_4$, latanoprost ethyl amide, 13,14 dihydro-15-keto-20-ethyl prostaglandin $F_{2\alpha}$ (unoprostone), 13,14 dihydro-15-keto-20-ethyl prostaglandin $F_{2\alpha}$ isopropyl ester (unoprostone isopropyl ester).

As already stated, the prostaglandin or prostaglandins may be combined with a second active substance, in particular with other classes of anti-glaucoma agents thus working together synergistically. They could, for example, be beta-blockers selected from the group including timolol maleate and carteolol chloride, carbonic anhydrase inhibitors such as those chosen from the group including dorzolamide chloride, or alpha-adrenergic agonists such as brimonidine tartrate. Examples of prostaglandin and beta-blocker combinations are:

Xalacom®—Pfizer: latanoprost 0.005%+timolol 0.5%,
Ganfort®—Allergan: bimatoprost 0.03%+timolol 0.5%
Duatrav®—Alcon: travoprost 0.004%+timolol 0.5%

In practice, the anti-glaucoma agent forms between 0.1 and 0.5% by weight of the solution.

It should be understood that the composition of the invention can contain usual additives with the exclusion of antimicrobial preservative agents. For example it could contain non-ionic agents for obtaining isotonicity such as polyols (e.g. glycerol, mannitol and sorbitol).

The formulation according to the invention can be presented in single use or multi-dose vials such as Abak®, Comod® or equivalent vials which allow supply of preservative-free ophthalmic solutions for several days.

Moreover, as already stated, the applicant has found that the ophthalmic solution according to the invention is stable relative to EP quality LDPE plastic packaging, corresponding to the European Pharmacopoeia definition and described in "Additive-free polyethylene for packaging sterile products".

The invention thus concerns a single or multi-dose vial produced in EP quality LDPE containing no additives filled with the ophthalmic solution previously described.

As the ophthalmic composition is in the form of a solution it can be sterilized by filtration at 0.2 μm on an appropriate membrane such as a PES or PVDF membrane. In addition, this property, combined with the stability of the product when packed in an LDPE container makes its manufacture compatible with BFS technology.

It is understood that the invention also concerns the use of the ophthalmic solution as previously described for producing a medicinal product for the treatment of glaucoma in humans or in animals, in particular for its ability to reduce intraocular pressure and/or provide neuroprotection for retinal tissues.

In practice, one drop of the ophthalmic solution is administered per day into each eye.

The invention also concerns a therapeutic treatment method for glaucoma in humans or animals consisting of instilling one drop per day of the previously described ophthalmic solution into each eye.

The invention and the advantages resulting from it are better illustrated by the following examples of embodiments and the figures attached.

DETAILED DESCRIPTION OF THE INVENTION

Example 1

Comparison of the Stabilizing Effect on Travoprost of Solutol® HS15 and Cremophor® EL 1—Solutol® HS15 Formulation

| Substance | Function | Composition per 100 g |
|---|---|---|
| Travoprost | Active substance | 0.004 g |
| PEG-15 hydroxystearate* | Solubilizer and stabilizer | 0.5 g |
| $Na_2HPO_4 \cdot 12H_2O$ | Buffer | 0.317 g |
| $NaH_2PO_4 \cdot 2H_2O$ | Buffer | 0.067 g |
| Sorbitol | Isotonicity agent | 4.5 g |
| EDTA | Antioxidant | 0.05 g |
| Purified water | Vehicle | qs 100 g |

*Solutol ® HS 15

2—Cremophor® EL Formulation

| Substance | Function | Composition per 100 g |
|---|---|---|
| Travoprost | Active substance | 0.004 g |
| PEG-35 Castor oil* | Solubilizer | 0.5 g |
| $Na_2HPO_4 \cdot 12H_2O$ | Buffer | 0.317 g |

-continued

| Substance | Function | Composition per 100 g |
|---|---|---|
| NaH$_2$PO$_4$•2H$_2$O | Buffer | 0.067 g |
| Sorbitol | Isotonicity agent | 4.5 g |
| EDTA | Antioxidant | 0.05 g |
| Purified water | Vehicle | qs 100 g |

*Trade name: Cremophor ® EL

3—Method of Preparing the Formulations

The water for injection was put into the stainless steel tank of the mixer.

It was sparged with nitrogen to eliminate the oxygen dissolved in the water as much as possible. Nitrogen inertion was maintained throughout the production process.

While stirring, the excipients were added and dissolved: isotonicity agent, buffer, antioxidant and solubilizer.

Each ingredient must be completely dissolved before adding the next substance.

While continuing to stir the active substance was added and dissolved.

When the mixture was totally homogeneous, the weight was adjusted with water for injection.

Sterilization filtration was performed using a PES or PVDF 0.2 μm filter under a current of nitrogen.

4—Packaging

The sterile solutions thus prepared were packed in LDPE plastic vials.

Figure 1:
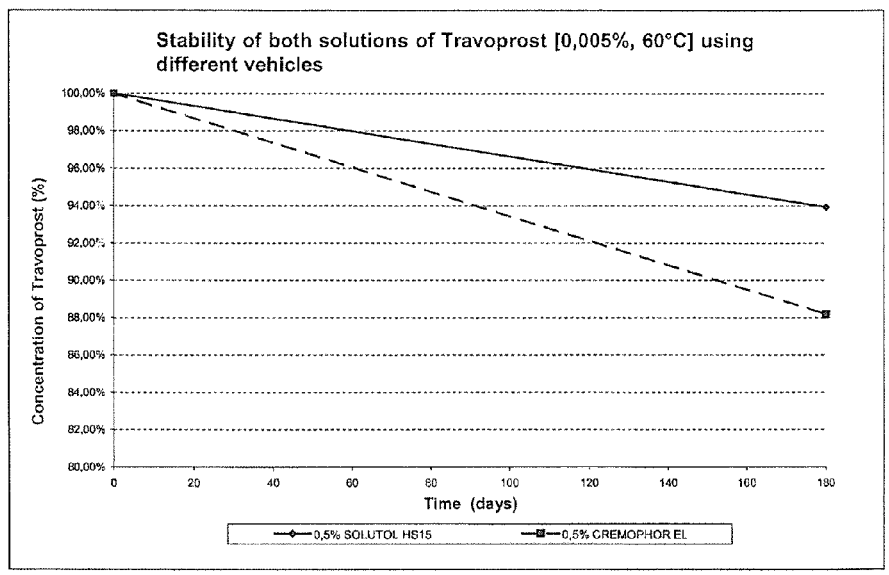
FIG. 1 compares the stabilizing effect on travoprost of Cremophor® EL and Solutol® HS15 at an identical concentration (0.5%).

As is shown in FIG. 1, at equal concentration the stabilizing effect on travoprost of Solutol® HS15 at a concentration of 0.004% was better than that of Cremophor®. In particular, after 180 days storage in a controlled atmosphere chamber at 60° C., the concentration of travoprost was 96% in the Solutol® HS15 formulation and only 88% in the Cremophor® EL formulation.

Example 2

Stability of Solutol® HS15 and Polysorbate 20 Formulations Containing Latanoprost The two formulations were compared:
1—Solutol® HS15 Formulation

| Substance | Function | Composition per 100 g |
|---|---|---|
| Latanoprost* | Active substance | 0.005 g |
| PEG-15 hydroxystearate* | Solubilizer and stabilizer | 0.5 g |
| Na$_2$HPO$_4$•12H$_2$O | Buffer | 0.317 g |
| NaH$_2$PO$_4$•2H$_2$O | Buffer | 0.067 g |
| Sorbitol | Isotonicity agent | 4.5 g |
| EDTA | Antioxidant | 0.05 g |
| Purified water | Vehicle | qs 100 g |

*Latanoprost as isopropyl ester
*Solutol ® HS 15

2—Polysorbate 20 Formulation

| Substance | Function | Composition per 100 g |
|---|---|---|
| Latanoprost (isopropyl ester) | Active substance | 0.005 g |
| Polysorbate 20* | Solubilizer | 2.0 g |
| Na$_2$HPO$_4$•12H$_2$O | Buffer | 0.317 g |
| NaH$_2$PO$_4$•2H$_2$O | Buffer | 0.067 g |
| Sorbitol | Isotonicity agent | 3.5 g |
| EDTA | Antioxidant | 0.05 g |
| Purified water | Vehicle | qs 100 g |

*Trade name: Montanox ® 20PHA

Figure 2:
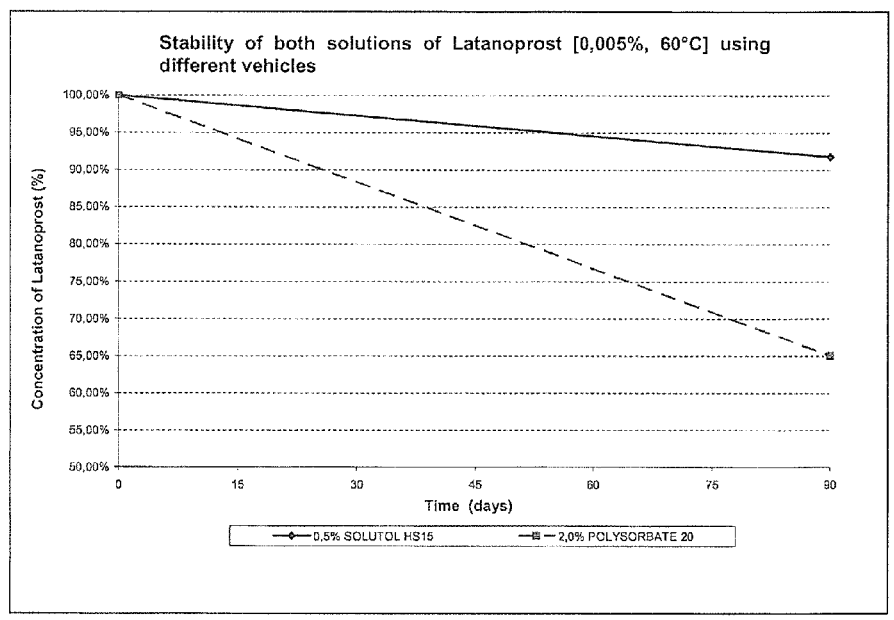
FIG. 2 compares the stabilizing effect on latanoprost of Solutol® HS15 (0.5%) and polysorbate 20 (2%).

As FIG. 2 shows, at a lower concentration (0.5% as against 2%). Solutol® HS 15 had a greater stabilizing effect on latanoprost than polysorbate 20. In particular, after 90 days storage in a controlled atmosphere chamber at 60° C., the residual latanoprost concentration was more than 90% in the case of the Solutol® HS 15 formulation, whereas it was only 65% in the polysorbate 20 formulation.

Example 3

Stability of Solutol® HS 15 and Polysorbate 80 Formulations Containing Latanoprost 1—Solutol® HS15 Formulation

| Substance | Function | Composition per 100 g |
|---|---|---|
| Latanoprost* | Active substance | 0.005 g |
| PEG-15 hydroxystearate* | Solubilizer and stabilizer | 0.5 g |
| Na$_2$HPO$_4$•12H$_2$O | Buffer | 0.317 g |
| NaH$_2$PO$_4$•2H$_2$O | Buffer | 0.067 g |
| Sorbitol | Isotonicity agent | 4.5 g |
| EDTA | Antioxidant | 0.05 g |
| Purified water | Vehicle | qs 100 g |

*Latanoprost as isopropyl ester
*Solutol ® HS 15

2—2% Polysorbate 80 Formulation

| Substance | Function | Composition per 100 g |
|---|---|---|
| Latanoprost (isopropyl ester) | Active substance | 0.005 g |
| Polysorbate 80* | Solubilizer | 2.0 g |
| Na$_2$HPO$_4$•12H$_2$O | Buffer | 0.317 g |
| NaH$_2$PO$_4$•2H$_2$O | Buffer | 0.067 g |
| Sorbitol | Isotonicity agent | 3.5 g |
| EDTA | Antioxidant | 0.05 g |
| Purified water | Vehicle | qs 100 g |

*Trade name Montanox ® 80 PHA

3—0.5% Polysorbate 80 Formulation

| Substance | Function | Composition per 100 g |
|---|---|---|
| Latanoprost (isopropyl ester) | Active substance | 0.005 g |
| Polysorbate 80* | Solubilizer | 0.5 g |
| Na$_2$HPO$_4$•12H$_2$O | Buffer | 0.317 g |
| NaH$_2$PO$_4$•2H$_2$O | Buffer | 0.067 g |
| Sorbitol | Isotonicity agent | 4.5 g |
| EDTA | Antioxidant | 0.05 g |
| Purified water | Vehicle | qs 100 g |

Figure 3:
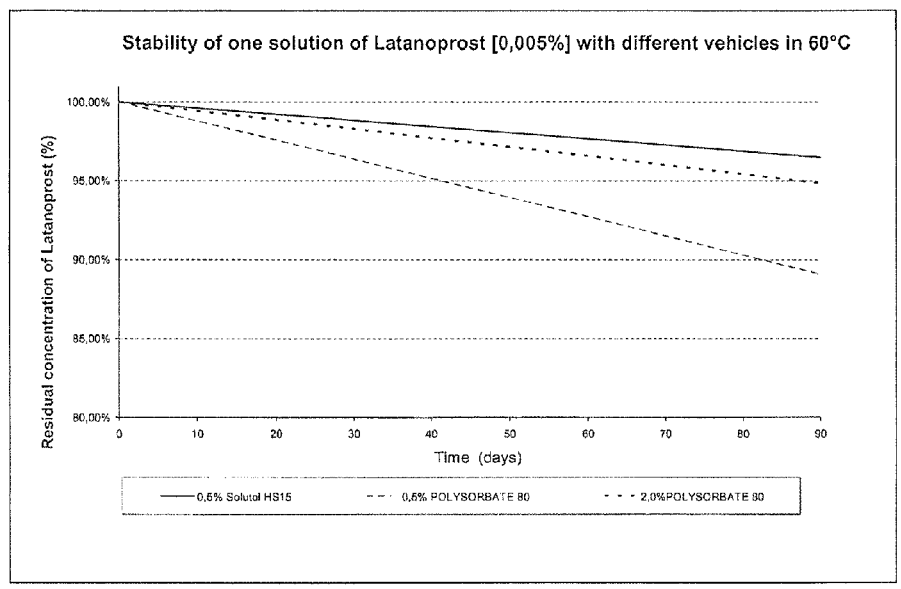
FIG. 3 compares the stabilizing effect on latanoprost of Solutol® HS15 (0.5%) and polysorbate 80 (2% and 0.5%).

As FIG. 3 shows, at a lower concentration (0.5% as against 2%), Solutol® HS had a greater stabilizing effect on latanoprost than polysorbate 80. After 90 days storage in a controlled atmosphere chamber at 60° C., the residual concentration of latanoprost was more than 90% in the case of the Solutol® HS15 formulation, i.e. above the limit required to consider the product as complying with the stability criterion.

For a concentration of polysorbate 80 of 2%, the residual concentration of latanoprost was also more than 90% but remained higher than that obtained in the presence of Solutol® HS15. In addition, this result was obtained with a greater polysorbate concentration than the concentration of Solutol® HS15. The 2% polysorbate formulation thus presents a greater risk of side effects than the Solutol® HS15 formulation.

For a polysorbate 80 concentration of 0.5%, the residual concentration of latanoprost was below 90%, which means that the product does not comply with the stability criterion.

Example 4

Stability at Ambient Temperature (25° C./40% RH) of the Solutol® HS15 Formulation Compared with a Formulation Containing Preservative (Xalatan®) in an EP Quality LDPE Vial In this study, two formulations were compared respectively:

Solutol® HS 15 Formulation

| Substance | Function | Composition per 100 g |
|---|---|---|
| Latanoprost* | Active substance | 0.005 g |
| PEG-15 hydroxystearate* | Solubilizer and stabilizer | 0.5 g |
| $Na_2HPO_4 \cdot 12H_2O$ | Buffer | 0.317 g |
| $NaH_2PO_4 \cdot 2H_2O$ | Buffer | 0.067 g |
| Sorbitol | Isotonicity agent | 4.5 g |
| EDTA | Antioxidant | 0.05 g |
| Purified water | Vehicle | qs 100 g |

*Latanoprost as isopropyl ester

*Solutol ® HS 15

Xalatan®—Marketed Product Containing 0.005% Latanoprost in the Form of its Isopropyl Ester and 0.02% Preservative (BAC)

| | Solutol formulation (preservative free) (=formulation A) | Xalatan ® formulation (with preservative/BAC) |
|---|---|---|
| Starting time | 100.0% | 100.0% |
| Time 6 month | 100.3% | 93.7% |

Figure 4:
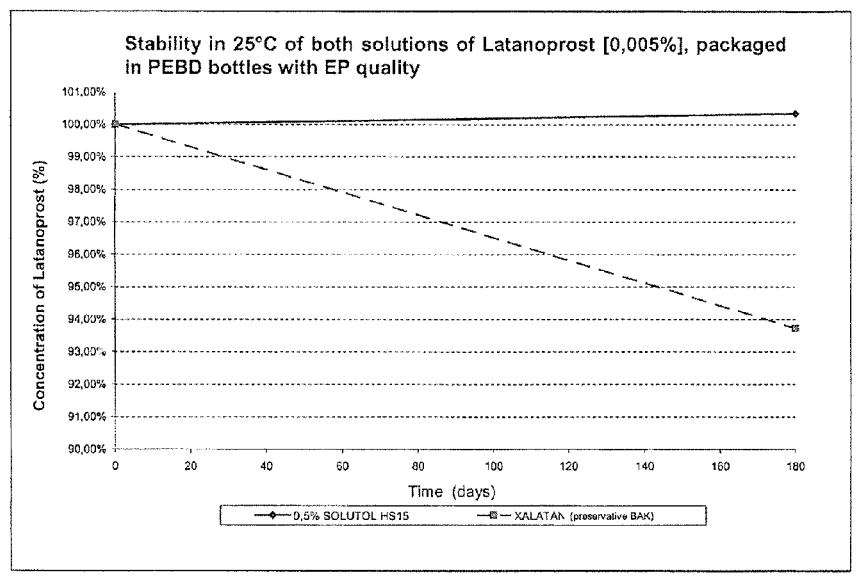
FIG. 4 compares the stabilizing effect of Solutol® HS15 (0.5%) with that of BAC (Xalatan® formulation).

As the above table and FIG. 4 show, the formulation with preservative was not stable at 25° C. in EP quality LDPE packaging. In contrast, the ophthalmic solution according to the invention can be marketed in packaging simply made in EP quality LDPE without the stability of the said solution being affected.

Example 5

0.1% Unoprostone Ophthalmic Solution

| Substance | Function | Composition per 100 g |
|---|---|---|
| Unoprostone* | Active substance | 0.1 g |
| PEG-15 hydroxystearate* | Solubilizer and stabilizer | 2.0 g |
| $Na_2HPO_4 \cdot 12H_2O$ | Buffer | 0.317 g |
| $NaH_2PO_4 \cdot 2H_2O$ | Buffer | 0.067 g |
| Sorbitol | Isotonicity agent | 3.5 |
| EDTA | Antioxidant | 0.05 g |
| Purified water | Vehicle | qs 100 g |

*Unoprostone as isopropyl

*Solutol ® HS 15

Example 6

Latanoprost+Timolol Ophthalmic Solution

| Substance | Function | Composition per 100 g |
|---|---|---|
| Latanoprost (isopropyl ester) | Active substance no 1 | 0.005 g |
| Timolol maleate | Active substance no 2 | 0.685 g |
| PEG-15 hydroxystearate* | Solubilizer and stabilizer | 0.5 g |
| $Na_2HPO_4 \cdot 12H_2O$ | Buffer | 0.317 g |
| $NaH_2PO_4 \cdot 2H_2O$ | Buffer | 0.067 g |
| Sorbitol | Isotonicity agent | 4.0 |
| EDTA | Antioxidant | 0.05 g |
| Purified water | Vehicle | qs 100 g |

*Solutol ® HS 15

Example 7

Latanoprost+Carteolol Ophthalmic Solution

| Substance | Function | Composition per 100 g |
|---|---|---|
| Latanoprost (isopropyl ester) | Active substance | 0.005 g |
| Carteolol (hydrochloride) | Active substance | 2.0 g |
| PEG-15-hydrostearate* | Solubilizer and stabilizer | 0.5 g |
| $Na_2HPO_4 \cdot 12H_2O$ | Buffer | 0.317 g |
| $NaH_2PO_4 \cdot 2H_2O$ | Buffer | 0.067 g |
| Sorbitol | Isotonicity agent | 3.0 |
| EDTA | Antioxidant | 0.05 g |
| Purified water | Vehicle | qs 100 g |

*Solutol ® HS 15

Example 8

Latanoprost+Dorzolamide Ophthalmic Solution

| Substance | Function | Composition per 100 g |
|---|---|---|
| Latanoprost (isopropyl ester) | Active substance no 1 | 0.005 g |
| Dorzolamide (HCl) | Active substance no 2 | 2.0 g |
| PEG-15-hydrostearate* | Solubilizer and stabilizer | 0.5 g |
| $Na_2HPO_4 \cdot 12H_2O$ | Buffer | 0.317 g |
| $NaH_2PO_4 \cdot 2H_2O$ | Buffer | 0.067 g |
| Sorbitol | Isotonicity agent | 3.0 |
| EDTA | Antioxidant | 0.05 g |
| Purified water | Vehicle | qs 100 g |

*Solutol ® HS 15

Example 9

Ocular Irritation Test Comparing Different Latanoprost Ophthalmic Solutions in Animals Aim of the Study:

An irritation test, the Draize test, was performed in the rabbit to assess the compatibility of two ophthalmic prostaglandin preservative-free formulations with the ocular surface.

Methodology:

The test was performed by comparison with a reference product, the compatibility of which with the ocular surface was considered to be acceptable: Xalatan®—a marketed ophthalmic solution. A negative control was also monitored (0.9% NaCl solution).

Protocol:

Various assessment criteria were recorded after several instillations of the test products. Twelve male albino rabbits (New Zealand White) were divided into groups of 3. Each group received several drops of ophthalmic solution into the right eye for 5 days according to the following schedule:

Day 1: 5 drops administered over 20 minutes.
Day 2: 5 drops administered over 20 minutes, twice a day
Day 3: 5 drops administered over 20 minutes, 4 times a day
Day 4: 5 drops administered over 20 minutes, 6 times a day
Day 5: 5 drops administered over 20 minutes, 8 times a day Quantity of product administered at each instillation: one drop of 50

The ocular evaluation was performed using an opthalmoscope and the Draize scale. Both eyes of each animal were observed. Readings were carried out as follows:

Day 1: before treatment (baseline), then 5 minutes, 30 minutes, 1 hour and 4 hours after the last instillation.

Day 2 to 5: just before the first instillation and 5 minutes after the last instillation of the day.

Results:

| | | Conjunctiva | | | | | |
|---|---|---|---|---|---|---|---|
| | | Redness | | Inflammation | | Discharge | |
| Treated eyes | | Day 1 | Days 2 to 5 | Day 1 | Days 2 to 5 | Day 1 | Days 2 to 5 |
| Formulation A (latanoprost 0.005% without preservative) | Mean | 0.0-1.0 | 0.0-0.3 | 0.0-0.0 | 0.0-0.0 | 0.0-0.0 | 0.0-0.0 |
| | Max score | 2 | 1 | 0 | 0 | 0 | 0 |
| | Number of animals with effect | 2/3 | 2/3 | 0/3 | 0/3 | 0/3 | 0/3 |
| Formulation B (travoprost 0.004% without preservative) | Mean | 0.3-1.0 | 0.0-1.0 | 0.0-0.0 | 0.0-0.0 | 0.0-0.3 | 0.0-0.0 |
| | Max score | 2 | 2 | 0 | 0 | 1 | 0 |
| | Number of animals with effect | 3/3 | 2/3 | 0/3 | 0/3 | 1/3 | 0/3 |
| Xalatan ® (latanoprost 0.005% with preservative) | Mean | 0.3-1.7 | 0.0-0.7 | 0.0-0.0 | 0.0-0.0 | 0.0-0.0 | 0.0-0.0 |
| | Max score | 2 | 1 | 0 | 0 | 0 | 0 |
| | Number of animals with effect | 3/3 | 2/3 | 0/3 | 0/3 | 0/3 | 0/3 |
| 0.9% NaCl (saline solution = control) | Mean | 0.0-0.0 | 0.0-0.3 | 0.0-0.0 | 0.0-0.0 | 0.0-0.0 | 0.0-0.0 |
| | Max score | 0 | 1 | 0 | 0 | 0 | 0 |
| | Number of animals with effect | 0/3 | 1/3 | 0/3 | 0/3 | 0/3 | 0/3 |

Latanoprost Preservative-Free Formulation:

After several repeated instillations into the right eye, the sum of conjunctival redness was 6/108 for the right eye and 0 for the left eye. The total conjunctival inflammation and total conjunctival discharge was 0 for each eye. The sum of effects on the cornea and iris was zero for each eye.

Travoprost Preservative-Free Formulation:

After several repeated instillations into the right eye, the sum of conjunctival redness was 11/108 for the right eye and 0 for the left eye. The total conjunctival inflammation was 0 for each eye. The total conjunctival discharge was 1/108 for the right eye and 0 for the left eye. The sum of effects on the cornea and iris was zero for each eye.

Latanoprost Formulation with Preservative (Reference/Xalatan®):

After several repeated instillations into the right eye, the sum of conjunctival redness was 18/108 for the right eye and 0 for the left eye. The total conjunctival inflammation and total conjunctival discharge was 0 for each eye. The sum of effects on the cornea and iris was zero for each eye.

Negative Control (0.9% NaCl Solution):

After several repeated instillations into the right eye, the sum of conjunctival redness was 1/108 for the right eye and 0 for the left eye. The total conjunctival inflammation and total conjunctival discharge was 0 for each eye. The sum of effects on the cornea and iris was zero for each eye.

Conclusion:

Following this protocol of several repeated instillations of different ophthalmic solutions into the right eye of albino rabbits over 5 days, the two prostaglandin formulations (without preservative) induced approximately the same ocular reactions, which were slightly less weaker than those obtained with the reference solution (Xalatan®). The results were considered to be valid given the response obtained with the negative control (saline solution). It can thus be concluded that under the study conditions, the two prostaglandin ophthalmic solutions (preservative free) show very good ocular tolerance.

Example 10

Comparative Study of the Ocular Pharmacokinetics in Pigmented Rabbits

Objective:

Comparison of the persistence of latanoprost (acid form) in two ocular tissues, after instillation of a single dose of two ophthalmic solutions containing a concentration of 0.005% (latanoprost isopropyl ester). Xalatan® ophthalmic solution is considered the reference product here. The aim of the study is to evaluate whether formulation A has an ocular kinetic profile equivalent to that of the reference product.

Methodology:

Study performed on two groups of 18 pigmented rabbits (Fauve de Bourgogne), after a single instillation of one drop of a 0.005% topical ophthalmic formulation of latanoprost into the right eye. The left eye is used as negative control. The first group received the preservative-free ophthalmic solution (Formulation A), while the second group received the reference product with preservative (Xalatan®). Size of the drop instilled: 50 μl. The quantity of latanoprost (acid form) was measured by HPLC-MS after extraction from two ocular tissues: the conjunctiva and cornea. Measurements were made at different times. 6 rabbits per group were tested at each time of analysis.

Results:

| Time (hours) | Formulation A (preservative free) | | Xalatan ® (reference with preservative) | |
| --- | --- | --- | --- | --- |
| | Cornea | Conjunctiva | Cornea | Conjunctiva |
| 0.5 | 100% | 100% | 100% | 100% |
| 6 | 5.3% +/− 5% | 1.0% +/− 5% | 5.5% +/− 5% | 1.2% +/− 5% |
| 24 | 0.2% +/− 5% | 0.3% +/− 5% | 0.1% +/− 5% | 0.2% +/− 5% |

Conclusion:

The ocular concentration kinetics of latanoprost after a single instillation of a drop of a 0.005% topical ophthalmic formulation were equivalent for the two products, in the study conditions.

The invention claimed is:

1. An ophthalmic solution without an antimicrobial preservative comprising as an active substance at least one prostaglandin and as a solubilizing agent, a surfactant wherein the solubilizing agent is polyoxyl-15-hydroxystearate.

2. The solution according to claim 1, wherein the concentration of the solubilizing agent in the solution is between 1 and 20 g/l.

3. The solution according to claim 1, wherein the prostaglandin concentration in the solution is between 0.02 and 1.5 g/l.

4. The solution according to claim 1 wherein the prostaglandin is selected from the group consisting of 17-phenyl-13,14 dihydro trinor prostaglandin $F_{2\alpha}$ isopropyl ester (latanoprost), 20-ethyl prostaglandin $F_{2\alpha}$, (+)-fluprostenol isopropyl ester (travoprost), 17-phenyl trinor prostaglandin $F_{2\alpha}$ amide, 17-phenyl-13,14 dihydro trinor prostaglandin $F_{2\alpha}$ ethyl amide (bimatoprost), tafluprost prostaglandin $F_{2\alpha}$ ethanolamide, bimatoprost (free acid)-$d_4$, bimatoprost-$d_4$, latanoprost ethyl amide, 13,14 dihydro-15-keto-20-ethyl prostaglandin $F_{2\alpha}$ (unoprostone), and 13,14 dihydro-15-keto-20-ethyl prostaglandin $F_{2\alpha}$ isopropyl ester (unoprostone isopropyl ester).

5. The solution according to claim 1, further comprising an antiglaucoma agent selected from the group consisting of beta-blockers, carbonic anhydrase inhibitors and alpha-adrenergic agonists.

6. The solution according to claim 5, wherein the antiglaucoma agent forms between 0.1 and 0.5% by weight of the solution.

7. The solution according to claim 1, further comprising an additive selected from the group consisting of isotonicity agents, antioxidants and buffer systems.

8. A single-use or multi-dose vial produced in additive-free LDPE containing the ophthalmic solution of claim 1.

9. A method of treating glaucoma, reducing intraocular pressure, or providing neuroprotection to retinal tissues in a human or animal in need thereof comprising administering to the human or animal a solution according to claim 1.

10. A method according to claim 9, comprising administering to the human or animal, via the topical route, one drop per day of the solution into each eye.

11. The solution according to claim 1, wherein the concentration of the solubilizing agent in the solution is between 2 and 10 g/l.

12. A method of treating glaucoma in an eye of a human in need thereof comprising topically administering to the eye of the human an effective amount of the solution according to claim 1.

13. A method of reducing intraocular pressure in an eye of a human in need thereof comprising topically administering to the eye of the human an effective amount of the solution according to claim 1.

14. A method of providing neuroprotection to retinal tissues in an eye of a human in need thereof comprising topically administering to the eye of the human an effective amount of the solution according to claim 1.

* * * * *